United States Patent
Dawood

[11] Patent Number: 5,898,112
[45] Date of Patent: *Apr. 27, 1999

[54] APPARATUS FOR TESTING THE PASSIVE FIT OF SCREW RETAINED STRUCTURES

[75] Inventor: Andrew Joseph Stanley Dawood, London, United Kingdom

[73] Assignee: Nobel Biocare AB, Gothenburg, Sweden

[ * ] Notice: This patent issued on a continued prosecution application filed under 37 CFR 1.53(d), and is subject to the twenty year patent term provisions of 35 U.S.C. 154(a)(2).

[21] Appl. No.: 08/525,626

[22] PCT Filed: Jan. 25, 1995

[86] PCT No.: PCT/IB95/00055

§ 371 Date: Dec. 21, 1995

§ 102(e) Date: Dec. 21, 1995

[87] PCT Pub. No.: WO95/20146

PCT Pub. Date: Jul. 27, 1995

[30] Foreign Application Priority Data

Jan. 25, 1994 [GB] United Kingdom .................... 9401332

[51] Int. Cl.⁶ .............................. B25B 23/14; G01L 3/02
[52] U.S. Cl. ..................................... 73/862.23; 73/862.193
[58] Field of Search ........................... 73/862.08, 862.23, 73/862.24, 862.25, 862.193, 761; 433/141, 174

[56] References Cited

U.S. PATENT DOCUMENTS

| | | |
|---|---|---|
| 3,892,146 | 7/1975 | Yasoshima . |
| 3,974,685 | 8/1976 | Walker . |
| 4,280,380 | 7/1981 | Eshghy . |
| 4,294,110 | 10/1981 | Whitehouse .......................... 73/862.23 |
| 4,314,490 | 2/1982 | Stone .................... 73/862.23 |
| 4,359,906 | 11/1982 | Cordey . |
| 4,397,196 | 8/1983 | Lemelson ............................. 73/862.23 |
| 4,558,601 | 12/1985 | Stasiek et al. ............................ 73/1 C |
| 4,759,225 | 7/1988 | Reynertson et al. . |
| 4,864,841 | 9/1989 | Heyaud ..................................... 73/1 C |
| 4,887,499 | 12/1989 | Kipfelsberger . |
| 4,926,700 | 5/1990 | Peplinski . |
| 4,982,612 | 1/1991 | Rittmann .............................. 73/862.23 |
| 5,154,242 | 10/1992 | Soshin et al. ...................... 73/862.331 |
| 5,158,458 | 10/1992 | Perry . |
| 5,402,688 | 4/1995 | Okada et al. ......................... 73/862.21 |
| 5,544,534 | 8/1996 | Fujitaka ................................ 73/862.23 |

*Primary Examiner*—Max H. Noori
*Attorney, Agent, or Firm*—Pollock, Vande Sande & Amernick

[57] ABSTRACT

A passivity indicating apparatus for use with structures to be joined by a threaded component including a tool for tightening the threaded component to at least one of the structures, the tool being driven by a motor; measuring device for measuring the change in torque over a time period delivered by the motor to the tool during tightening; indicator receiving output from the measuring device of the change in torque over the time period and indicating precision of fit between the structures.

6 Claims, 2 Drawing Sheets

APPARATUS FOR TESTING THE PASSIVE FIT OF SCREW RETAINED STRUCTURES

FIELD OF THE INVENTION

There are many situations where a screw retained structure must fit against another structure to which it is to be connected with a high degree of accuracy and passivity—i.e., is as the retaining screws are tightened, there should be no stress or strain induced in either structure.

This invention relates to an apparatus for checking whether screw retained structures fit passively. There are numerous situations where structures must be precisely and passively joined by screws, bolts, or other threaded components, over a wide range of accuracy and torque. This invention has a particular application in dentistry, as described below, but the governing principles can equally be applied in any other class of engineering application.

BACKGROUND OF THE INVENTION

Where teeth have been lost, as a result of, for example, dental disease, it may become necessary to install dental implants. Dental implants are usually made of titanium or other bio-compatible materials, and form a strong inflexible union with bone. This type of union has been termed "osseointegration". It is now understood that osseointegration will endure for many years in favorable circumstances. However this union may rapidly break down if the implant is overloaded by unfavorable forces.

It is common practice to use several implants to support a dental bridge. It is also common practice to use retaining screws to connect such bridges to the implants.

Bridges are presently fabricated by casting wax or plastic patterns in dental alloys, or by using computer aided design and computer aided milling technology. Most stages of construction are carried out on models prepared from impressions of the patient's mouth. There is thus a great potential for error in the fabrication of the bridge framework, and so it is not surprising that small discrepancies in the mechanical fit of the bridge superstructure to the dental implants arise.

When positioned in the mouth a small discrepancy may sometimes go unnoticed with the result that, when the bridge is screwed into place, in spite of a small error in fit, flexure of the implant, surrounding bone, bridge superstructure, retaining screen, and any other prosthetic components may permit the bridge to be seated in spite of the imperfect fit. As a result of this flexure, there may then be a considerable build up of stress or strain in the system. This later manifests itself, as failure of one of the components, or failure of osseointegration and ultimately the loss of the implant.

When the implant supported bridge superstructure fits against the implants precisely it is commonly said to fit "passively" that is, when the screws are tightened no stress or strain is introduced. Under these circumstances, tightening the screws that retain the bridge superstructure merely compresses the framework against the head of the implant.

The rapid increase in torque as the retaining screws arc tightened when the screw head contacts the bridge superstructure, and the superstructure fits the implants passively is illustrated in FIG. 1.

Where the implant retained bridge superstructure fits the implants poorly, tightening the retaining screws results in a relatively slower build up of tension in the screw as the various components of the system are flexed.

The tension in (or torque applied to) the retaining screw increasing slowly as the various components of the system are flexed, and then rapidly as the superstructure is compressed against the implant when the superstructure finally contacts the implant is shown in FIG. 2.

SUMMARY OF INVENTION

The present invention is a device which monitors the build up of tension in the retaining screw as it is tightened. A rapid build up in tension, with minimal rotation of the retaining screw, indicates that a bridge superstructure fits the implants passively, whereas a relatively slow build up in tension with prolonged rotation of the screw as the tension increases, indicates that the superstructure is initially separated from the implant.

DESCRIPTION OF THE PREFERRED EMBODIMENTS

Figure 1:
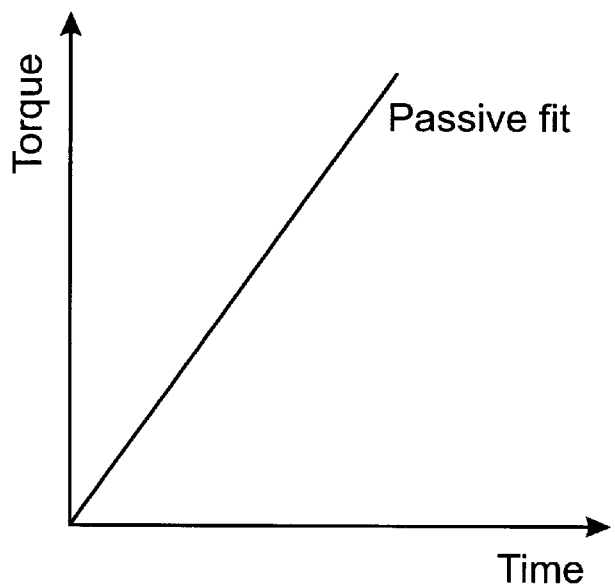
FIGS. 1 and 2 illustrate a comparison of the relationship between torque change over time for a passive fit and an imprecise fit.
Figure 2:
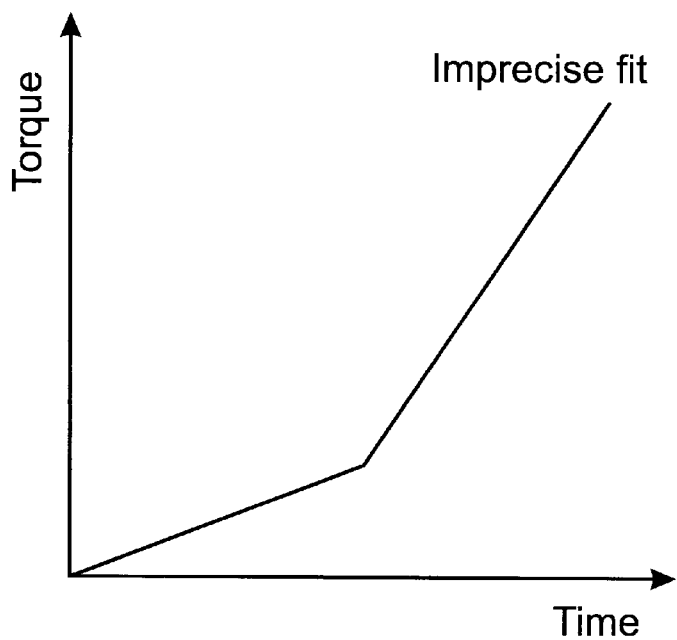
Figure 3:
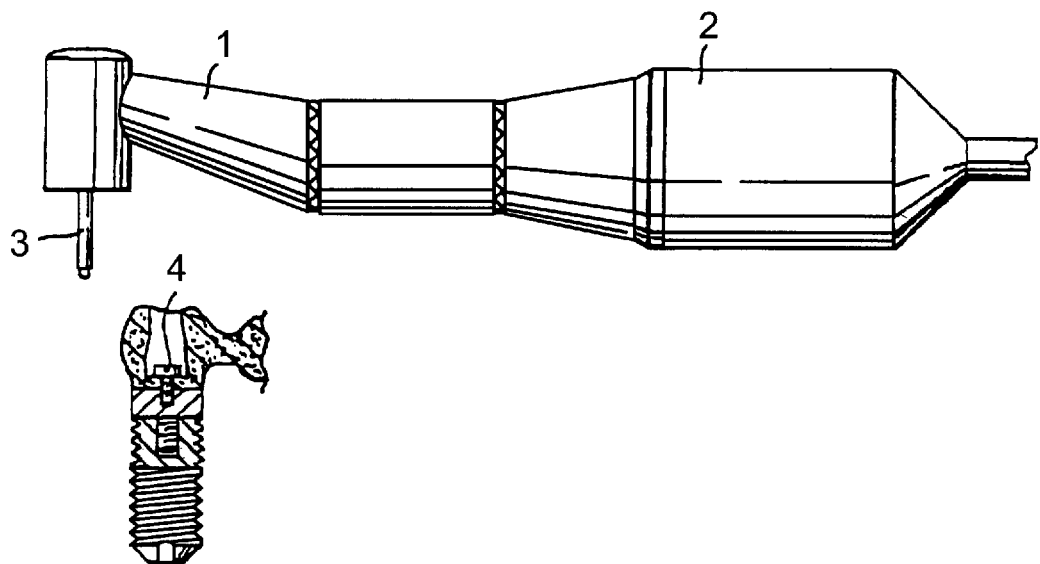
FIGS. 3 and 4 illustrate a specific embodiment of this invention indicating apparatus.

FIG. 3 shows a conventional, or dedicated, dental handpiece 1 is powered by a miniature electric motor (micro-motor) 2. An appropriate screw-driving attachment 3 is loaded in the handpiece to permit its use for tightening a retention screw 4.

Figure 4:
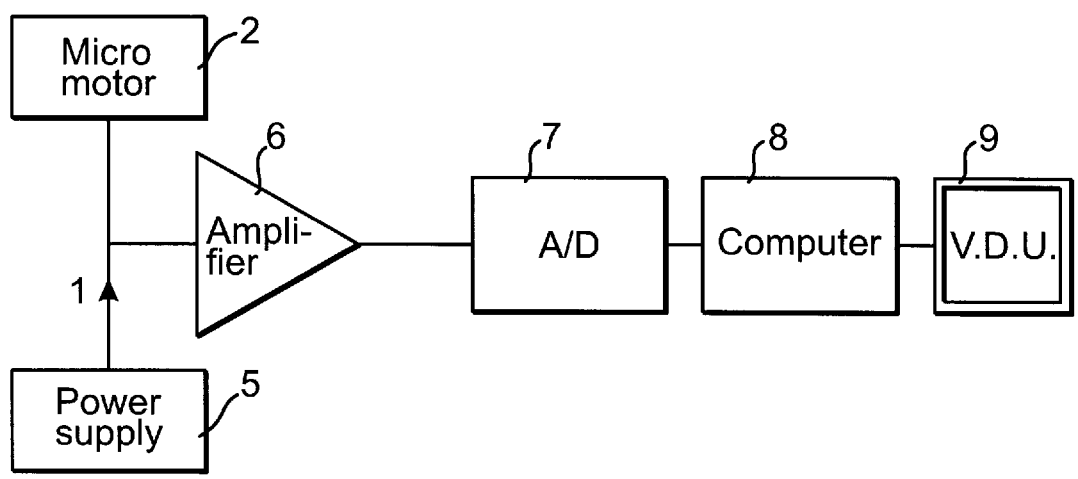

FIG. 4 shows a diagram illustrating that, power to the micro-motor 2 is regulated by the power supply 5 such that voltage is maintained at a constant level, and current may be monitored by appropriate circuitry. The handpiece and micro-motor are calibrated such that current in the power supply to the micro-motor is correlated with the torque delivered by the handpiece as it tightens the retaining screw.

In a preferred embodiment of the invention, an analogue to digital converter 7 samples the current to the micro-motor after current to voltage conversion and appropriate amplification 6. The digital output is then processed by a microcomputer 8 which then displays a graphic representation of a curve of current (torque) against time on a visual display 9; the shape of the curve may then be qualitatively assessed. Further processing will also return a numerical result, such as rate of chance in torque.

Alternatively circuitry monitors the rate of change in current as the retaining screw is tightened. A rapidly increasing current indicative of a passively fitting superstructure is indicated by an indicator light, e g a green light emitting diode. Below a predetermined threshold other indicators illuminate, thus demonstrating various levels of inadequacy of fit. Similarly, a numerical display may be provided.

The instrument may be calibrated by using the apparatus first upon standardized structures alone with the desired retention screw. This will also permit comparison of the fit of the bridge when seated on the model with the fit when seated in the patient's mouth.

An alternative embodiment of this invention may employ components such as optical encoders or Hall effect sensors, or other types of transducers, in conjunction with appropriate circuitry, or may employ circuitry which monitors fluctuations induced in the supply to the micro-motor by the motor, which permits the rotation of the micro-motor to be monitored.

The number of rotations, or parts of rotations of the motor correlates with the rotation of the screw driving head, and, this, can be counted as the torque delivered to the retaining screw increases. As torque builds up over a specified range, the number of rotations of the micro-motor counted over the specified range is inversely related to the accuracy of the fit of the structures.

The result of the test may be displayed numerically, or may be indicated by indicating lights which illuminate at appropriate thresholds. The instrument may be calibrated by using the apparatus first upon standardized bridge frameworks and models with the appropriate retention screws, and will also permit comparison of the bridge when seated on the model with the bridge when seated in the patient's mouth.

In both these embodiments, signal processing and other processing functions may be carried out with the aid of a micro computer and associated software. This facilitates the calibration process and permits comparison of the digital data derived from the analogue to digital converter from measurements carried out on a patient, with measurements carried out on a standardized bridge framework, or with the patient's bridge framework when seated on the model upon which it was fabricated. This will also facilitate compensation for play or friction in the system which may result in increasing current in the motor, or rotation of an element of the apparatus, prior to actual rotation of the retaining screw.

I claim:

1. A method for determining a precision of fit between dental structures to be joined by a threaded component, said method comprising the steps of:

tightening said threaded component to said dental structures;

measuring a torque applied to said threaded component during said tightening during a period of time;

determining the precision of fit between said dental structures based on a variation in a rate of change in said torque during said period of time; and indicating the precision of fit between said dental structures in a visual display.

2. The method according to claim 1, wherein said measuring and determining are performed with electronic circuitry.

3. The method according to claim 1, further comprising the step of:

counting a number of rotations of said threaded component over a specified range of torque.

4. The method according to claim 1 wherein said determining step comprises:

detecting a passive fit between said dental structures when said rate of change in said torque is substantially constant during said predetermined period of time; and detecting an imprecise fit between said dental structures when said rate of change of said torque varies during said predetermined period of time.

5. A method of determining a precision of fit between dental structures to be joined by a threaded component, said method comprising the steps of:

tightening said threaded component with a dental handpiece supplied with a constant voltage to join said dental structures;

measuring a torque applied to said threaded component during a predetermined period of time during said tightening;

determining a minimum threshold of torque which indicates a precise fit between said dental structures;

visually indicating said precision of fit between said dental structures based on said measured torque and said minimum threshold.

6. The method of claim 5 wherein the step of visually indicating further comprises indicating various levels of an imprecise fit based on a difference between said measured torque and said minimum threshold.

* * * * *